(12) United States Patent
Kubo

(10) Patent No.: US 9,565,399 B2
(45) Date of Patent: Feb. 7, 2017

(54) ENDOSCOPE SYSTEM, PROCESSOR DEVICE THEREOF, AND IMAGE PROCESSING METHOD

(71) Applicant: FUJIFILM Corporation, Tokyo (JP)

(72) Inventor: Masahiro Kubo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 264 days.

(21) Appl. No.: 14/013,301

(22) Filed: Aug. 29, 2013

(65) Prior Publication Data

US 2014/0063216 A1  Mar. 6, 2014

(51) Int. Cl.
*H04N 7/18* (2006.01)
*A61B 1/06* (2006.01)
*G06T 5/50* (2006.01)
*A61B 1/00* (2006.01)
*A61B 5/00* (2006.01)
*A61B 5/1455* (2006.01)
*A61B 5/1459* (2006.01)

(52) U.S. Cl.
CPC ............. *H04N 7/18* (2013.01); *A61B 1/00009* (2013.01); *A61B 1/0638* (2013.01); *G06T 5/50* (2013.01); *A61B 5/0084* (2013.01); *A61B 5/1459* (2013.01); *A61B 5/14551* (2013.01); *A61B 5/7425* (2013.01); *G06T 2207/10068* (2013.01); *G06T 2207/10152* (2013.01); *G06T 2207/20221* (2013.01); *G06T 2207/30004* (2013.01)

(58) Field of Classification Search
CPC .................................. A61B 1/00045
USPC ............................. 348/71, 65, 68
See application file for complete search history.

(56) References Cited

U.S. PATENT DOCUMENTS

2012/0157768 A1* 6/2012 Saito .................. A61B 1/00009
   600/109
2013/0018242 A1* 1/2013 Yamaguchi .......... A61B 1/0638
   600/339

FOREIGN PATENT DOCUMENTS

| EP | 2 465 433 A1 | 6/2012 |
| EP | 2 545 852 A1 | 1/2013 |
| JP | 2011-92690 A | 5/2011 |

OTHER PUBLICATIONS

Extended European Search Report, dated Dec. 18, 2013, for Patent Application No. 13181438.6.

* cited by examiner

*Primary Examiner* — Jamie Atala
*Assistant Examiner* — Masum Billah
(74) *Attorney, Agent, or Firm* — Birch, Stewart, Kolasch & Birch, LLP

(57) ABSTRACT

In an oxygen saturation level measurement mode, a color image sensor images an internal body portion alternately irradiated with measurement light and normal light. A normal image is produced from image data obtained under irradiation with the normal light. An oxygen saturation level is calculated from image data obtained under irradiation with the measurement light. Based on the oxygen saturation level, a hyperoxic region and a hypoxic region are determined in the normal image. A color balance process and a color enhancement process are applied to the hyperoxic region to improve visibility of depressions and projections of internal body tissue and a blood vessel pattern. A gain process is applied to the hypoxic region to make distinct color variations according to the degree of the oxygen saturation level.

11 Claims, 16 Drawing Sheets

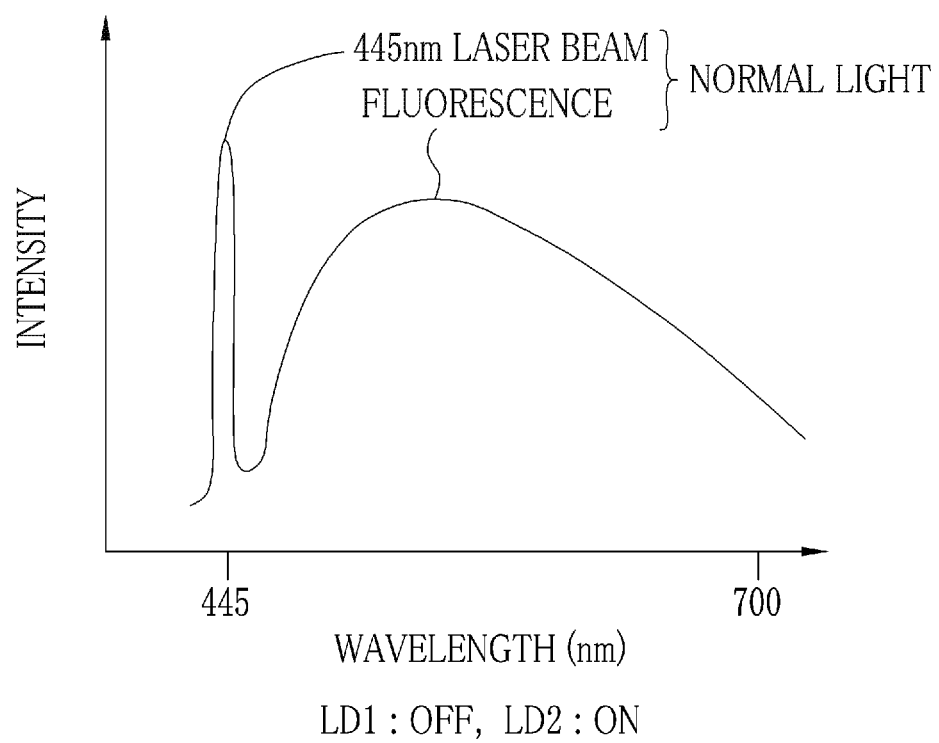

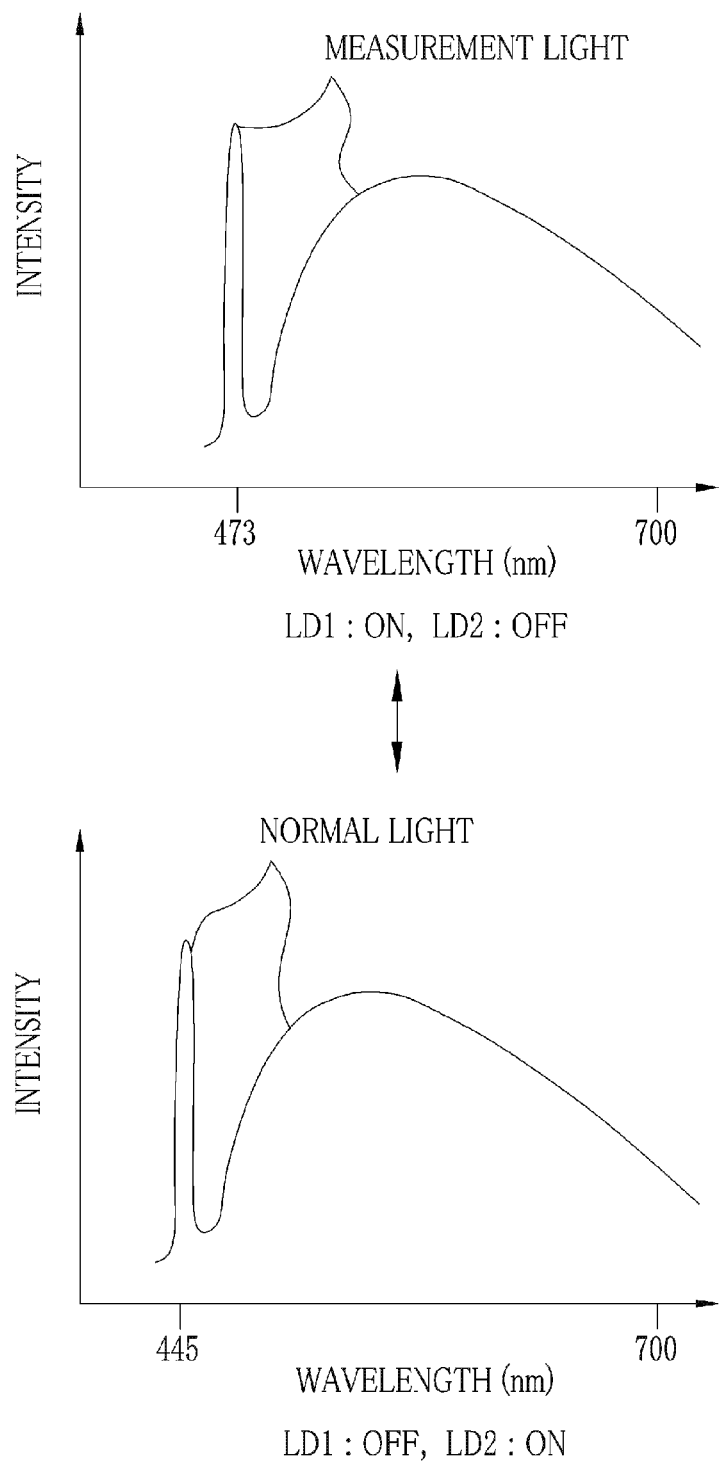

BLUE IMAGE DATA B2

93a    93b

| | | WB PROCESS | GAIN PROCESS | COLOR ENHANCEMENT PROCESS |
|---|---|---|---|---|
| FIRST REGION PROCESS | HYPOXIC REGION | X | O | X |
| | HYPEROXIC REGION | O | X | O |
| SECOND REGION PROCESS | HYPOXIC REGION | X | O | O |
| | HYPEROXIC REGION | O | X | X |
| THIRD REGION PROCESS | HYPOXIC REGION | X | O | O |
| | HYPEROXIC REGION | O | X | O |

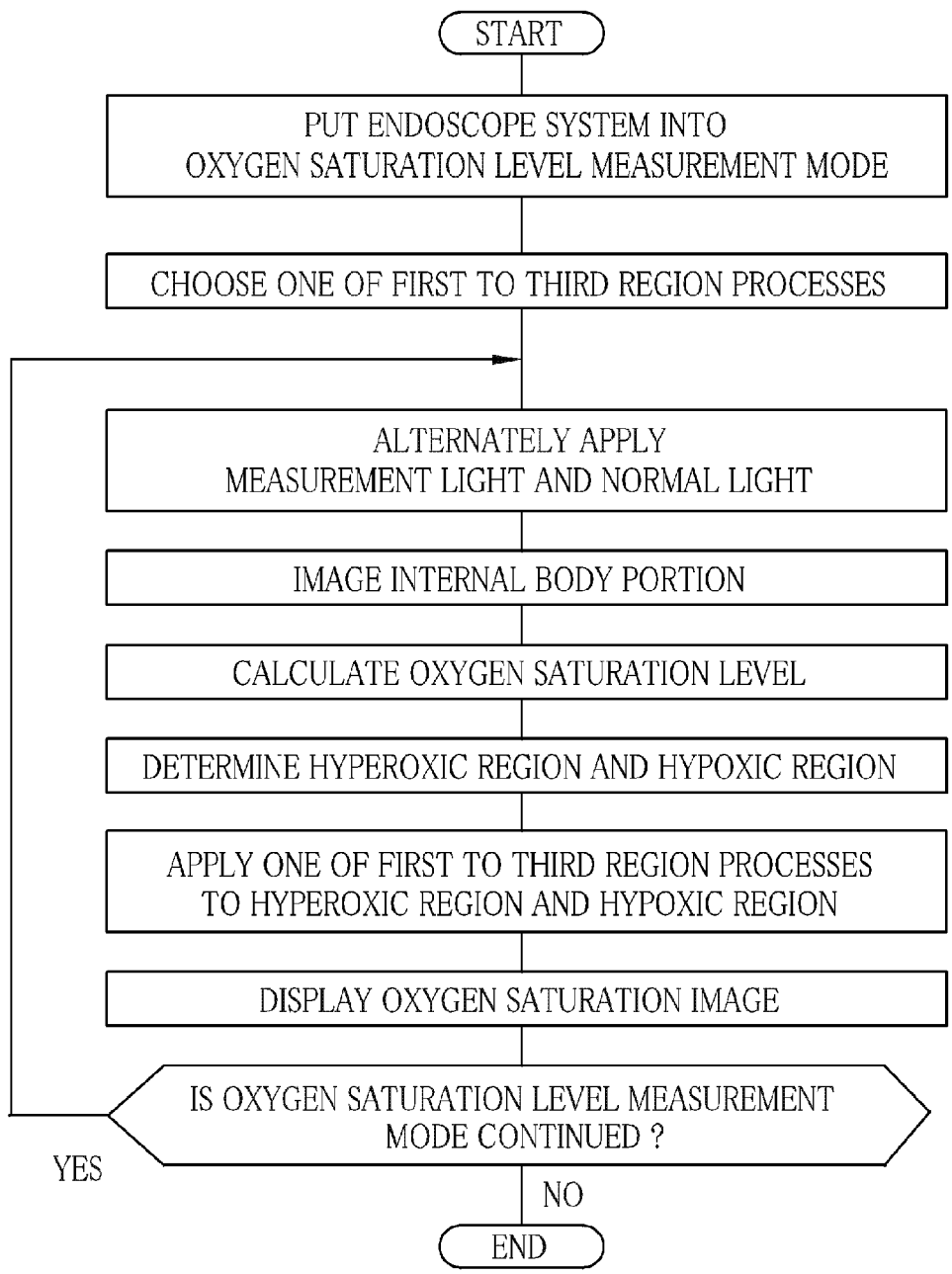

ENDOSCOPE SYSTEM, PROCESSOR DEVICE THEREOF, AND IMAGE PROCESSING METHOD

BACKGROUND OF THE INVENTION

1. Field of the Invention

The present invention relates to an endoscope system that images an oxygen saturation level of blood, a processor device of the endoscope system, and an image processing method.

2. Description Related to the Prior Art

In a medical field, an endoscope system is widely used for diagnosis and treatment. The endoscope system is constituted of a light source device, an endoscope device, a processor device, a monitor device, and an input device. In use of the endoscope system, an insert section of the endoscope device is introduced into a patient's body. An internal body portion is imaged by an image sensor provided at a distal end portion of the insert section, while being applied with illumination light from the distal end portion. There is also known an endoscope system that obtains various types of living body information from an image captured with the use of specific narrow band light as the illumination light.

According to US Patent Application Publication No. 2012/0157768 (corresponding to Japanese Patent Laid-Open Publication No. 2012-139482), for example, an endoscope system produces an oxygen saturation image (special image), which images an oxygen saturation level of blood, with the use of narrow band light having a wavelength range in which oxyhemoglobin and deoxyhemoglobin have different absorption coefficients as the illumination light. In this oxygen saturation image, a hyperoxic region having an oxygen saturation level of 60% or more is displayed with the same color as a normal image, which is obtained under irradiation with white light. A hypoxic region having an oxygen saturation level of less than 60% is displayed with artificial colors in accordance with the degree of the oxygen saturation level. Since the hypoxic region being a lesion-suspected portion and the hyperoxic region being a normal portion are colored differently, it is possible to grasp the distribution of a lesion at first sight.

Furthermore, this oxygen saturation image can indicate variations in the oxygen saturation level in the hypoxic region by difference in color among the artificial colors. On the other hand, the hyperoxic region is colorfully displayed just as with the normal image, and hence facilitates obtaining living body information useful for diagnosis, e.g. a blood vessel pattern and projections and depressions of a mucosal surface. Therefore, for the purpose of improving accuracy in diagnosis using the oxygen saturation image, it is demanded to increase visibility of living body tissue in the hyperoxic region and comprehensibility of the degree of the oxygen saturation level in the hypoxic region.

SUMMARY OF THE INVENTION

An object of the present invention is to provide an endoscope system that improves visibility of living body tissue in a hyperoxic region and comprehensibility of the degree of an oxygen saturation level in a hypoxic region, a processor device of the endoscope system, and an image processing method.

To achieve the above and other objects, an endoscope system according to the present invention includes a lighting section, an image information obtaining section, a normal image producing section, an oxygen saturation level calculator, a region determiner, and a region processor. The lighting section applies illumination light to an object. Broad band light in a visible range and narrow band light having a wavelength range in which oxyhemoglobin and deoxyhemoglobin have different absorption coefficients are used as the illumination light. The image information obtaining section images the object under irradiation with the broad band light to obtain first image information, and images the object under irradiation with the narrow band light to obtain second image information. The normal image producing section produces a normal image having a wavelength component of the broad band light based on the first image information. The oxygen saturation level calculator calculates an oxygen saturation level of blood based on the second image information. The region determiner determines in the normal image a hyperoxic region having the oxygen saturation level of a predetermined value or more and a hypoxic region having the oxygen saturation level of less than the predetermined value. The region processor applies different types of processes to the hyperoxic region and the hypoxic region, and produces an oxygen saturation image.

It is preferable that the endoscope system further includes a monitor device for displaying the normal image or the oxygen saturation image.

The region processor preferably applies a color balance process to the hyperoxic region to adjust color balance, and applies a gain process to the hypoxic region to bring about color variations in the hypoxic region in accordance with difference in the oxygen saturation level.

The color balance process may adjust white balance in the hyperoxic region by adjustment of a pixel value of the hyperoxic region. The gain process may vary color in the hypoxic region in accordance with a degree of the oxygen saturation level by adjustment of the pixel value of the hypoxic region.

The region processor may apply a color enhancement process to at least one of the hyperoxic region and the hypoxic region.

The color enhancement process to be applied to the hyperoxic region may be a red color enhancement process for enhancing a red component.

The hypoxic region may be tinged with artificial colors different in accordance with the degree of the oxygen saturation level, and the color enhancement process to be applied to the hypoxic region is an artificial color enhancement process for enhancing the artificial colors.

The image information obtaining section may include a color image sensor. The first image information may include first blue image data, first green image data, and first red image data. The color image sensor may image the object under irradiation with first blue narrow band light of 440 to 460 nm and fluorescence produced by wavelength conversion of the first blue narrow band light by a wavelength conversion element, and B pixels, G pixels, and R pixels of the color image sensor may produce the first blue, green, and red image data, respectively. The second image information may include second blue image data. The color image sensor may image the object under irradiation with second blue narrow band light of 460 to 480 nm and fluorescence produced by wavelength conversion of the second blue narrow band light by the wavelength conversion element, and the B pixels of the color image sensor may produce the second blue image data.

The image information obtaining section may include a monochrome image sensor. The first image information may include first blue image data, first green image data, and first red image data. The monochrome image sensor may image the object sequentially irradiated with blue light, green light, and red light to obtain the first blue image data, the first green image data, and the first red image data, respectively. The second image information may include second blue image data. The monochrome image sensor may image the object under irradiation with blue light of 450 to 500 nm to obtain the second blue image data.

The oxygen saturation level calculator may calculate the oxygen saturation level based on the second blue image data, the first green image data, and the first red image data.

A processor device of an endoscope system according to the present invention includes a reception section, an oxygen saturation level calculator, a region determiner, and a region processor. The reception section receives the first and second image information. The normal image producing section produces a normal image having a wavelength component of the broad band light based on the first image information. The oxygen saturation level calculator calculates an oxygen saturation level of blood based on the second image information. The region determiner determines in the normal image a hyperoxic region having the oxygen saturation level of a predetermined value or more and a hypoxic region having the oxygen saturation level of less than the predetermined value. The region processor applies different types of processes to the hyperoxic region and the hypoxic region, and produces an oxygen saturation image.

An image processing method of an endoscope system includes the steps of producing a normal image having a wavelength component of broad band light based on first image information; calculating an oxygen saturation level of blood based on second image information; determining in the normal image a hyperoxic region having an oxygen saturation level of a predetermined value or more and a hypoxic region having the oxygen saturation level of less than the predetermined value; and applying different types of processes to the hyperoxic region and the hypoxic region, and producing an oxygen saturation image.

According to the present invention, since the color balance process is applied to the hyperoxic region of the normal image, the visibility of the hyperoxic region e.g. projections and depressions of living body tissue is improved. On the other hand, the hypoxic region is subjected to the gain process in accordance with the oxygen saturation level, instead of the color balance process. Thus, the degree of the oxygen saturation level is represented by color in the hypoxic region. This allows grasping the degree of the oxygen saturation level at first sight.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 3A is a graph showing an emission spectrum of normal light;
FIG. 3B shows graphs of emission spectra of measurement light and the normal light.

FIG. 16 is a flowchart in the oxygen saturation measurement mode.

DESCRIPTION OF THE PREFERRED EMBODIMENTS (First Embodiment)

Figure 1:
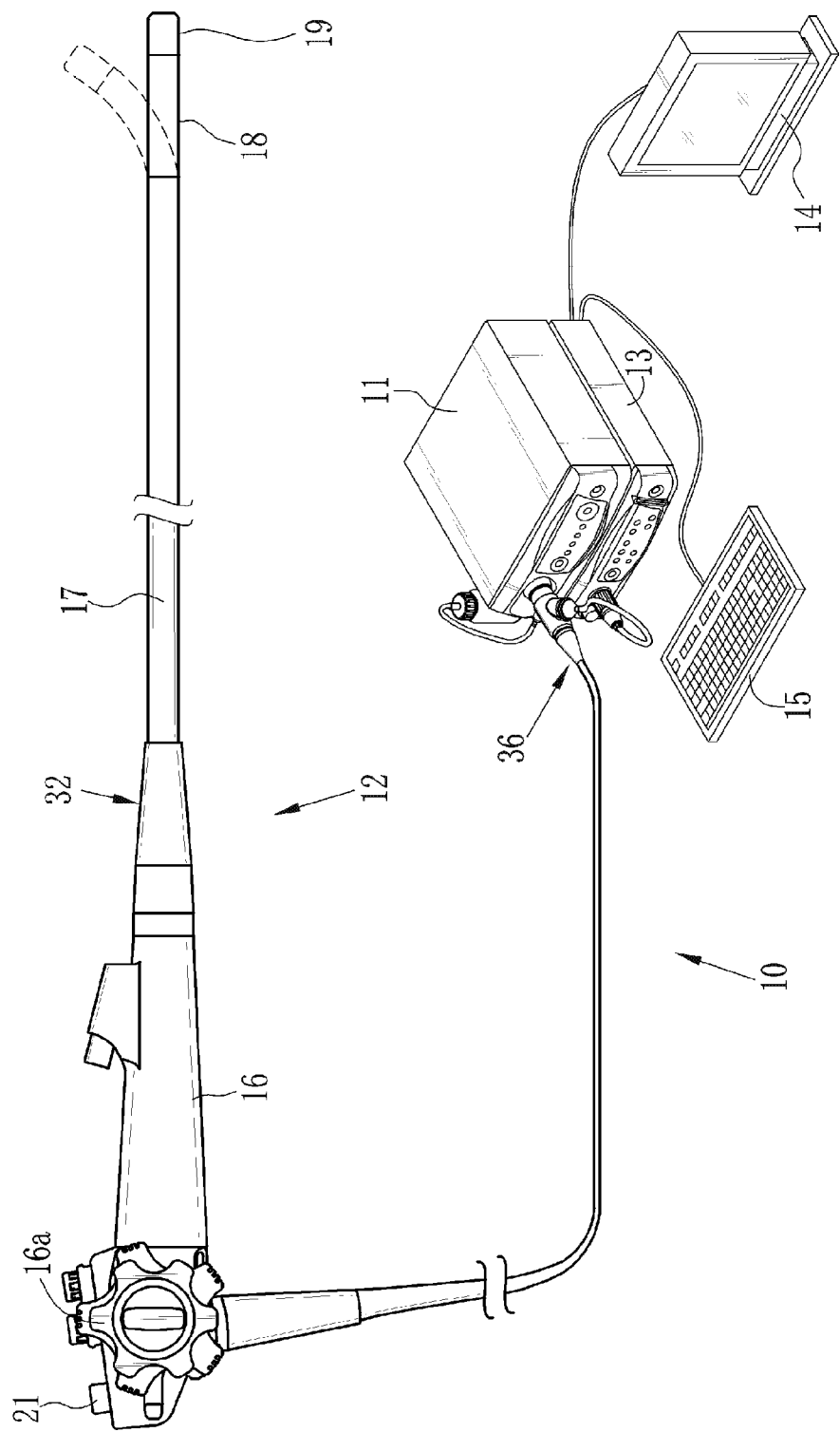
FIG. 1 is a schematic view of an endoscope system.

As shown in FIG. 1, an endoscope system 10 is constituted of a light source device 11, an endoscope device 12, a processor device 13, a monitor device 14, and an input device 15 including a keyboard and the like. The light source device 11 emits illumination light to irradiate an interior of a patient's body. The endoscope device 12 images an internal body portion irradiated with the illumination light emitted from the light source device 11. The processor device 13 applies image processing to an image signal obtained by the endoscope device 12. An endoscopic image obtained by the image processing is displayed on the monitor device 14.

The endoscope device 12 includes a flexible elongated portion 17, a steering assembly 18, and a head assembly 19 provided in this order from the side of a control handle unit 16. The flexible elongated portion 17 is slender and bendable. The steering assembly 18 is curved by a turn of an angle knob 16a provided on the control handle unit 16. Turning the steering assembly 18 to an arbitrary direction and an arbitrary angle makes the head assembly 19 aim at a desired body portion to be examined.

The endoscope system 10 is switchable between a normal mode and an oxygen saturation level measurement mode (special mode) for observing an oxygen saturation level of blood. In the normal mode, a normal image, which is captured under irradiation with visible light having a wavelength band ranging from blue to red, is displayed on the monitor device 14. In the oxygen saturation level measurement mode, an oxygen saturation image, which images an oxygen saturation level of blood, is displayed on the monitor device 14. Mode switching is performed by the input device 15 or a mode switch 21 provided in the endoscope device 12.

Figure 2:
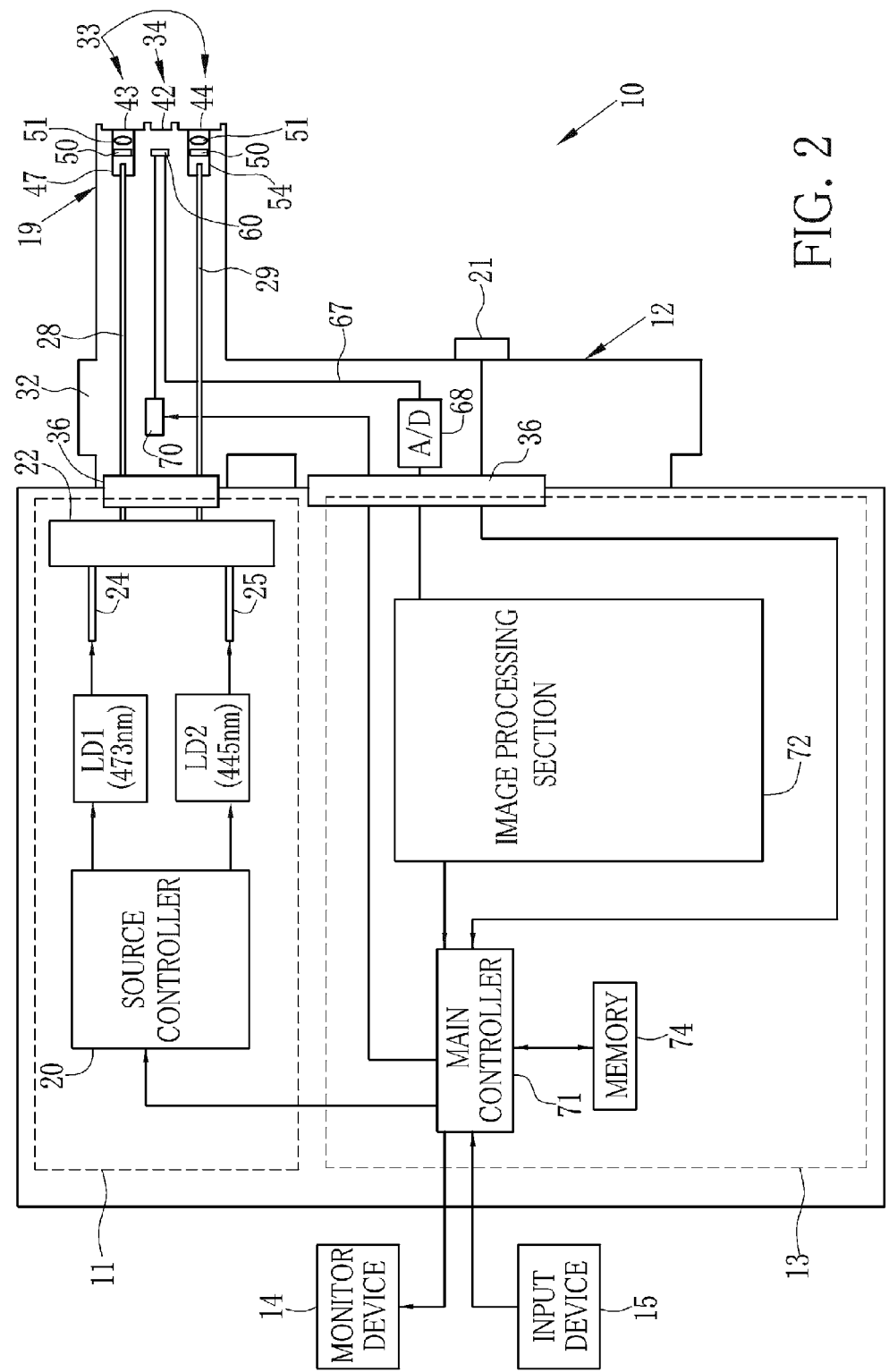
FIG. 2 is a block diagram of the endoscope system according to a first embodiment.

As shown in FIG. 2, the light source device 11 is provided with two types of laser sources LD1 and LD2 and a source controller 20. The laser source LD1 emits a first laser beam having a central wavelength of 473 nm. A part of the first laser beam is converted into green to red fluorescence by a phosphor (wavelength conversion element) 50 disposed in the head assembly 19 of the endoscope device 12. The laser source LD2 emits a second laser beam having a central wavelength of 445 nm. As with the first laser beam, a part of the second laser beam is converted into fluorescence by the phosphor 50. The first and second laser beams emitted from the laser sources LD1 and LD2 enter optical fibers 24 and 25, respectively, through condenser lenses (not shown).

The first laser beam preferably has a wavelength band of 460 to 480 nm. The second laser beam preferably has a wavelength band of 440 to 460 nm. As the laser sources LD1 and LD2, a broad-area type InGaN laser diode, InGaNAs laser diode, GaNAs laser diode, or the like is available.

The source controller 20 controls the laser sources LD1 and LD2. When the laser source LD1 is turned on, measurement light is applied, which includes the fluorescence emitted from the phosphor 50 excited by the first laser beam and the first laser beam passed through the phosphor 50 without being absorbed. When the laser source LD2 is turned on, normal light is applied, which includes the fluorescence emitted from the phosphor 50 excited by the second laser beam and the second laser beam passed through the phosphor 50 without being absorbed. In the normal mode, as shown in FIG. 3A, the laser source LD2 is turned on, while the laser beam LD1 is turned off. Thus, the normal light is applied to the internal body portion. In the oxygen saturation level measurement mode, as shown in FIG. 3B, the laser sources LD1 and LD2 are alternately turned on and off. Thus, the measurement light and the normal light are applied in an alternate manner to the internal body portion.

As shown in FIG. 2, a coupler 22 branches the first or second laser beam transmitted from the optical fiber 24 or 25 in two beams, and enters the branched two beams into light guides 28 and 29, respectively. Each light guide 28 or 29 is made of a fiber bundle, being a bundle of a number of optical fibers.

The endoscope device 12 being an electronic endoscope is provided with a lighting section 33, an imaging section 34, and a connector 36. The lighting section 33 applies two beams of light led through the light guides 28 and 29 to the internal body portion. The imaging section 34 captures an image of the internal body portion. The connector 36 detachably connects the endoscope device 12 to the light source device 11 and the processor device 13.

The lighting section 33 has two lighting windows 43 and 44 disposed on both sides of the imaging section 34. The light passed through the phosphor 50 is applied to the internal body portion through the lighting windows 43 and 44. The imaging section 34 has an imaging window 42 positioned at approximately the center of the head assembly 19. The light reflected from the internal body portion is captured through the imaging window 42.

Light projection units 47 and 54 are disposed in the recess of the lighting windows 43 and 44, respectively. In each of the light projection units 47 and 54, the first or second laser beam is incident upon the phosphor 50 to emit the fluorescence. The first or second laser beam and the emitted fluorescence are applied to the internal body portion through a lens 51.

The phosphor 50 contains a plurality of types of fluorescent substances (for example, a YAG-based fluorescent substance or BAM ($BaMgAl_{10}O_{17}$)) that absorb a part of the first and second laser beams and emit the green to red fluorescence. The entrance of the first laser beam into the phosphor 50 produces the pseudo white measurement light, by mixing of the green to red fluorescence emitted from the phosphor 50 and the first laser beam passed through the phosphor 50 without being absorbed. The entrance of the second laser beam into the phosphor 50 produces the pseudo white normal light, by mixing of the green to red fluorescence emitted from the phosphor 50 and the second laser beam passed through the phosphor 50 without being absorbed.

The phosphor 50 preferably has an approximately rectangular parallelepiped shape. In this case, the phosphor 50 may be formed by compacting the fluorescent substances by a binder into the rectangular parallelepiped shape. The mixture of the fluorescent substances and resin such as inorganic glass may be formed into the rectangular parallelepiped shape. The phosphor 50 is known under the trademark of Micro White (MW).

In the recess of the imaging window 42, there is provided an optical system such as an objective lens unit (not shown) for capturing image light of the internal body portion. An image sensor 60 e.g. a CCD (charge coupled device) is provided behind the objective lens unit to image the internal body portion. An IT (interline transfer) type CCD is used as the image sensor 60 in this embodiment, but a CMOS (complementary metal-oxide semiconductor) having a global shutter may be used instead.

Figure 4A:
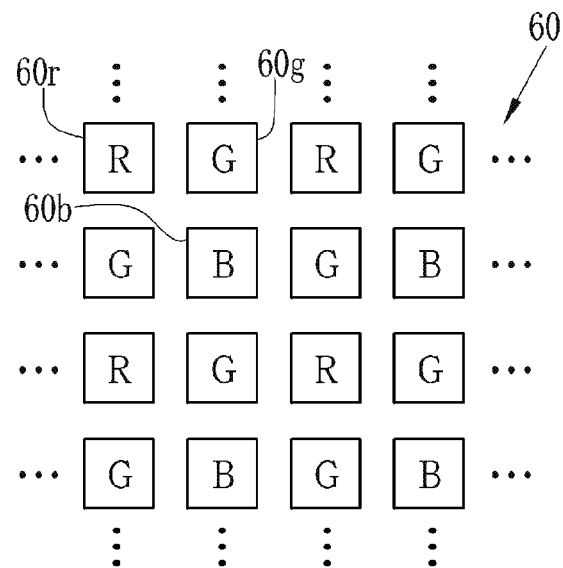
FIG. 4A is a plan view showing a layout of B, G, and R pixels in a color image sensor.
Figure 4B:
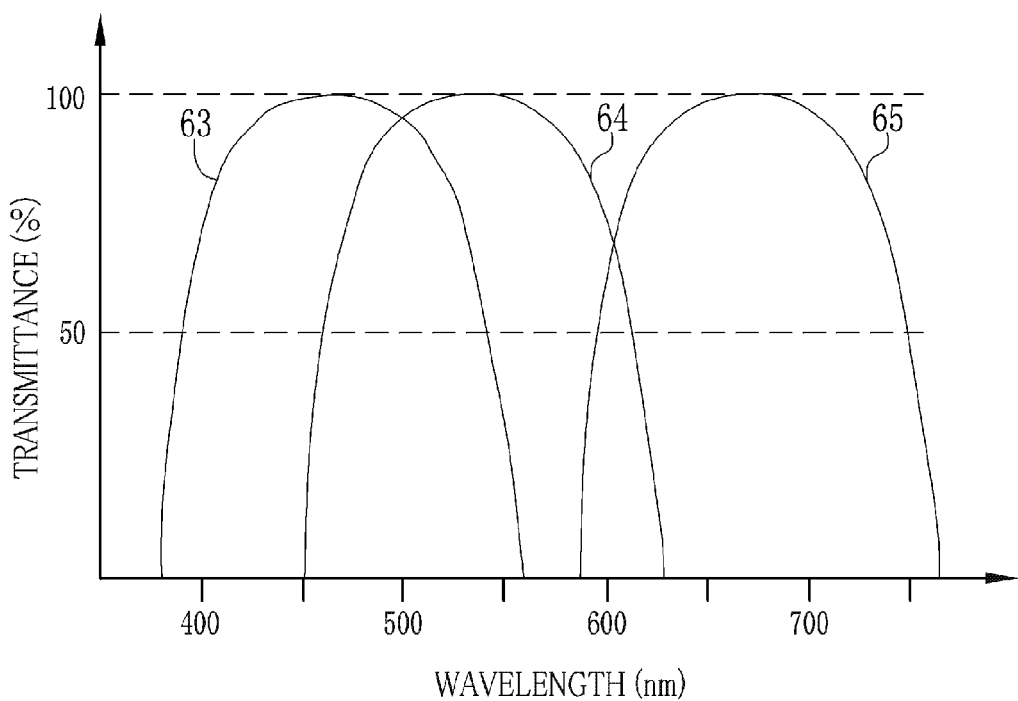
FIG. 4B is a graph showing spectral transmittance of B, G, and R color filters.

The image sensor 60 receives the light from the objective lens unit at its light receiving surface (imaging surface), and performs photoelectric conversion of the received light to output an analog image signal. The image sensor 60 is a color CCD. In the light receiving surface, as shown in FIG. 4A, pixel groups each of which consists of one B pixel 60b having a blue filter, two G pixels 60g having a green filter, and one R pixel 60r having a red filter are arranged into a matrix. The blue, green, and red filters have high spectral transmittance in a blue wavelength band, a green wavelength band, and a red wavelength band, as represented by curves 63, 64, and 65 of FIG. 4B, respectively.

As shown in FIG. 2, the analog image signal outputted from the image sensor 60 is inputted to an A/D converter 68 through a scope cable 67. The A/D converter 68 converts the analog image signal into digital image data in accordance with its voltage level. The converted image data is inputted to the processor device 13 through the connector 36.

Figure 5A:
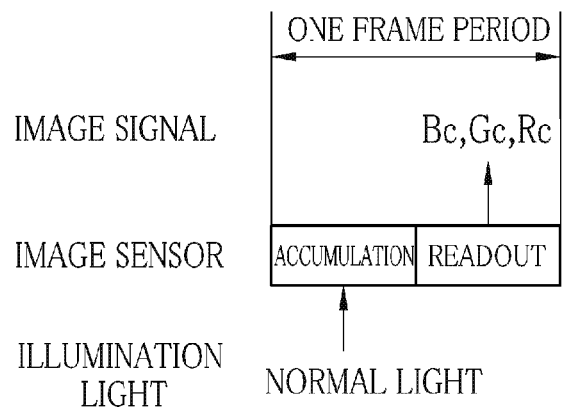
FIG. 5A is an explanatory view of the operation of the image sensor in a normal mode in the first embodiment.

An imaging controller 70 controls the image sensor 60 in accordance with the mode of the endoscope system 10. In the normal mode, as shown in FIG. 5A, the internal body portion is imaged under irradiation with the normal light. In one frame period, a step of accumulating electric charge in the image sensor 60 and a step of reading out blue, green, and red signals from the B, G, and R pixels of the image sensor 60 are performed. These steps are repeated as long as the endoscope system 10 is in the normal mode. The A/D converter 68 converts the blue, green, and red signals into blue, green, and red image data Bc, Gc, Rc, respectively.

Figure 5B:
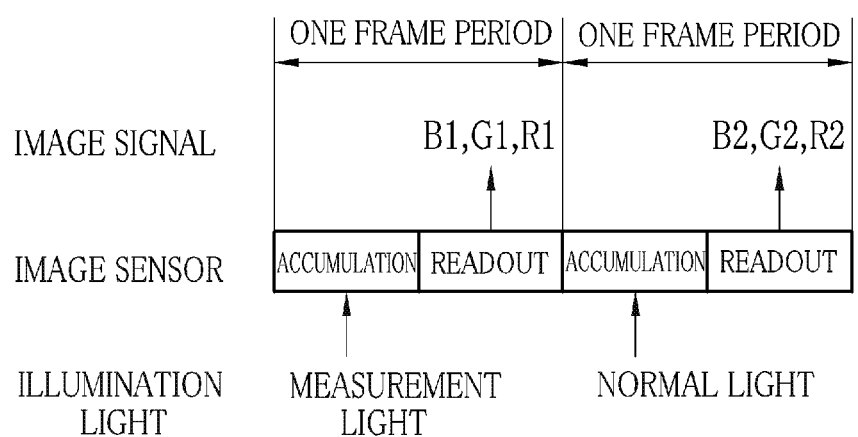
FIG. 5B is an explanatory view of the operation of the image sensor in an oxygen saturation measurement mode in the first embodiment.

In the oxygen saturation level measurement mode, as shown in FIG. 5B, the internal body portion is imaged under irradiation with the measurement light in a first frame period. A step of accumulating electric charge in the image sensor 60 and a step of reading out blue, green, and red signals from the B, G, and R pixels of the image sensor 60 are performed under irradiation with the measurement light. After that, in a second frame period, the internal body portion is imaged under irradiation with the normal light. A step of accumulating electric charge in the image sensor 60 and a step of reading out blue, green, and red signals from the B, G, and R pixels of the image sensor 60 are performed under irradiation with the normal light. This two-frame period operation is repeated as long as the endoscope system 10 is in the oxygen saturation level measurement mode.

The A/D converter 68 converts the blue, green, and red signals obtained in the first frame period into blue, green, and red image data B1, G1, and R1 respectively. Note that, the blue image data B1 corresponds to second blue image data included in second image information. The A/D converter 68 converts the blue, green, and red signals obtained in the second frame period into blue, green, and red image data B2, G2, and R2, respectively. Note that, the blue image data B2 corresponds to first blue image data included in first image information. The green image data G2 corresponds to first green image data included in the first image information. The red image data R2 corresponds to first red image data included in the first image information.

As shown in FIG. 2, the processor device 13 is provided with a main controller 71, an image processing section 72, and a memory 74. The monitor device 14 and the input device 15 are connected to the main controller 71. The main controller 71 controls the operation of each component of the processor device 13, and furthermore controls the operation of the source controller 20 of the light source device 11, the imaging controller 70 of the endoscope device 12, and the monitor device 14 based on information inputted from the input device 15 and the mode switch 21 of the endoscope device 12.

Figure 6:
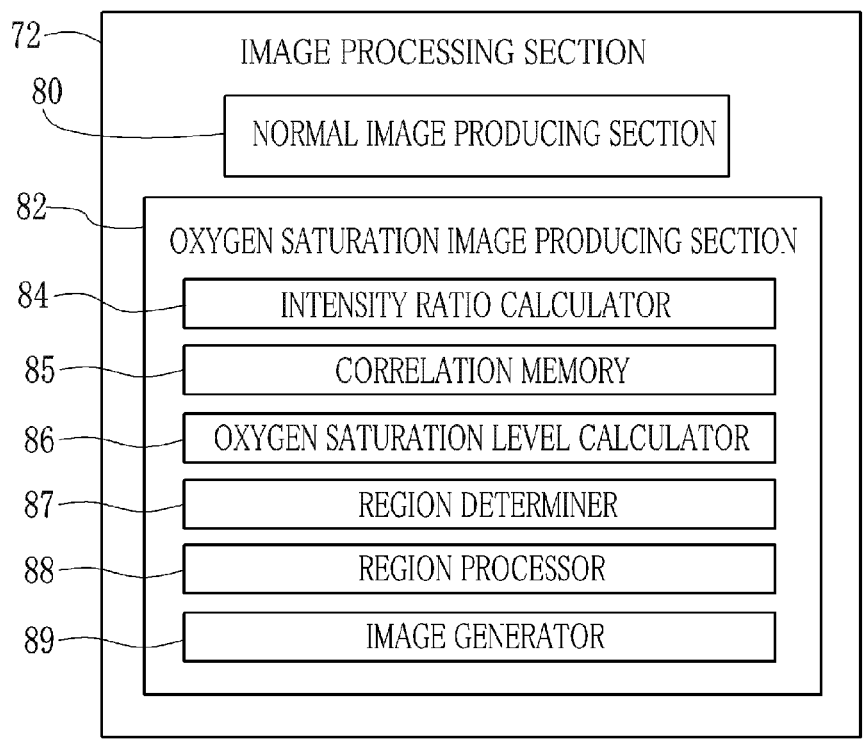
FIG. 6 is a block diagram of an image processing section.

As shown in FIG. 6, the image processing section 72 includes a normal image producing section 80 and an oxygen saturation image producing section 82. The normal image producing section 80 assigns the blue, green, and red image data Bc, Gc, and Rc obtained in the normal mode to B, G, and R channels of the monitor device 14, respectively. Thus, a normal image is displayed on the monitor device 14.

The oxygen saturation image producing section 82 includes an intensity ratio calculator 84, a correlation memory 85, an oxygen saturation level calculator 86, a region determiner 87, a region processor 88, and an image generator 89. The intensity ratio calculator 84 calculates the intensity ratio B1/G2 between the blue image data B1 and the green image data G2 and the intensity ratio R2/G2 between the red image data R2 and the green image data G2 out of the image data obtained in the oxygen saturation level measurement mode. The intensity ratio calculator 84 calculates the intensity ratios of the identical pixel between the two frames of image data. The intensity ratios may be calculated with respect to every pixel of the image data, or only the pixels of a blood vessel area. The blood vessel area is determined based on the difference in a pixel value between the pixel of the blood vessel area and the pixel of the other area.

The correlation memory 85 stores the correlation among the oxygen saturation level and the intensity ratios B1/G2 and R2/G2.

Figure 7:
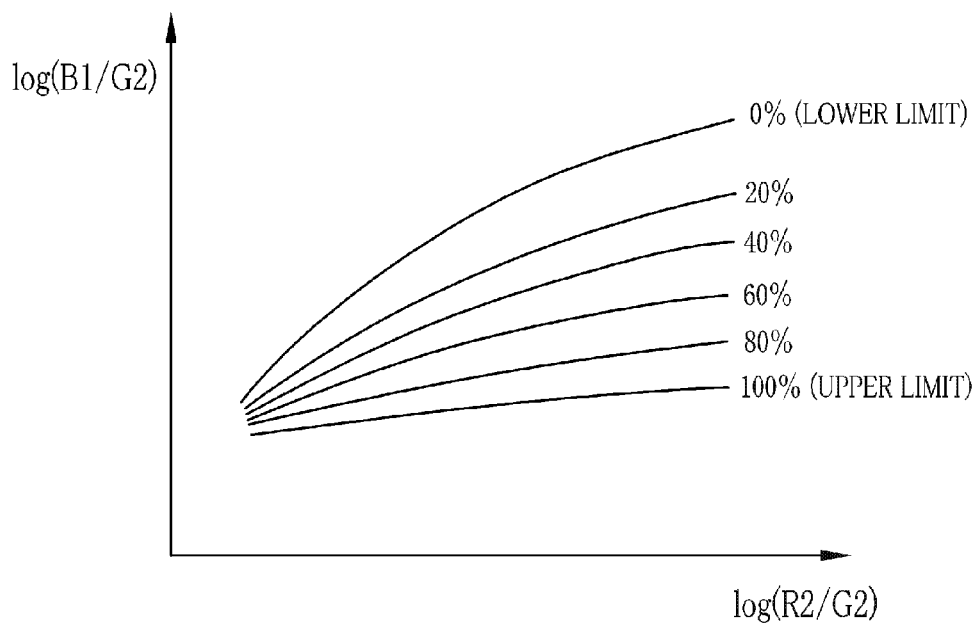
FIG. 7 is a graph showing the correlation among an oxygen saturation level and intensity ratios B1/G2 and R2/G2.

This correlation is in the form of a two dimensional table, as shown in FIG. 7, in which contour lines representing the oxygen saturation level are defined in two-dimensional space. The position and shape of the contour lines are determined by physical simulation of light scattering, and variable in accordance with blood volume. For example, the variation of the blood volume widens or narrows the distance between the two adjacent contour lines. The intensity ratios B1/G2 and R2/G2 are in a log scale.

Figure 8:
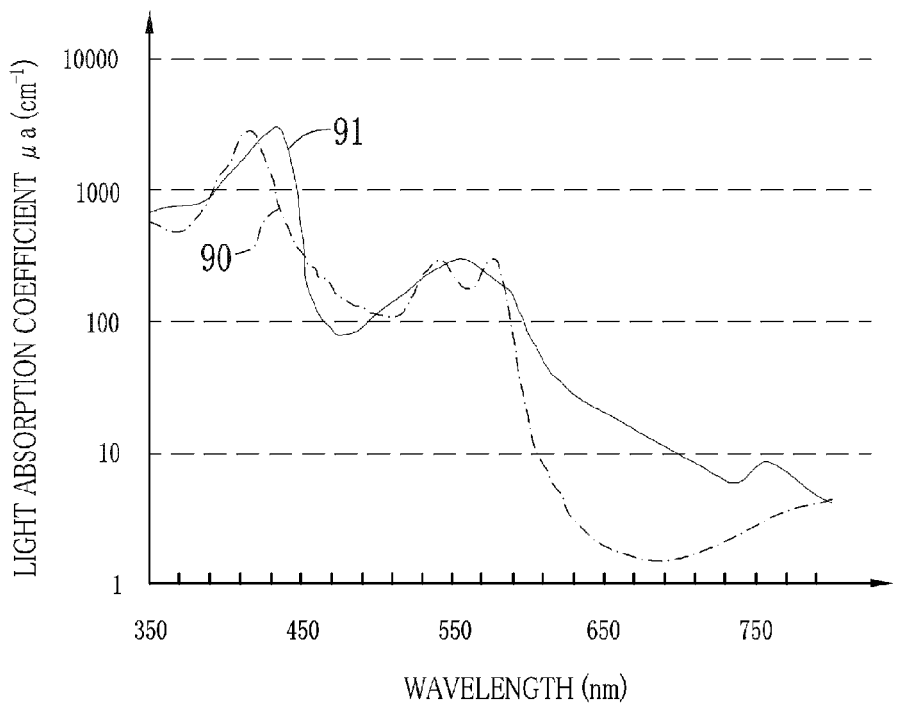
FIG. 8 is a graph showing an absorption coefficient of oxyhemoglobin and deoxyhemoglobin in a wavelength band of 350 to 800 nm.

The correlation closely relates to an absorption property of oxyhemoglobin and deoxyhemoglobin and a light scattering property. Referring to FIG. 8, a curve 90 represents an absorption coefficient of oxyhemoglobin, and a curve 91 represents an absorption coefficient of deoxyhemoglobin. For example, using a wavelength of 473 nm at which the absorption coefficient largely differs between oxyhemoglobin and deoxyhemoglobin allows easy obtainment of information about the oxygen saturation level. However, the blue image data B1 including a signal corresponding to light of 473 nm is highly dependent not only on the oxygen saturation level but also on the blood volume. For this reason, the use of the intensity ratios B1/G2 and R2/G2, which are calculated from the blue image data B1, the red image data R2 mainly depending on the blood volume, and the green image data G2 being a reference signal (standardization signal) of the blue image data B2 and the red image data R2, allows obtainment of the oxygen saturation level with high accuracy with eliminating the influence of the blood volume.

Light having a wavelength band of 470 to 700 nm has a small scattering coefficient and little wavelength dependence in mucosal tissue. Thus, using the light of this wavelength band as the illumination light allows obtainment of blood information, including the blood volume and the oxygen saturation level, with reducing the influence of the depth of a blood vessel.

Note that, the correlation memory 85 may also store the correlation between the blood volume and the intensity ratio R2/G2. This correlation is in the form of a one dimensional table in which the blood volume increases with increase in the intensity ratio R2/G2. The correlation between the blood volume and the intensity ratio R2/G2 is used for calculating the blood volume.

The following three items hold true according to wavelength dependence of the absorption coefficient of hemoglobin:

(1) In the vicinity of a wavelength of 470 nm (for example, a blue wavelength range having a central wavelength of 470±10 nm), the absorption coefficient largely varies in accordance with variation in the oxygen saturation level.

(2) In a green wavelength range between 540 and 580 nm, a mean value of the absorption coefficient is hardly susceptible to the oxygen saturation level.

(3) In a red wavelength range between 590 and 700 nm, the absorption coefficient seems to vary largely in accordance with the oxygen saturation level, but in actual fact, is hardly susceptible to the oxygen saturation level because a value of the absorption coefficient itself is very small.

The reason why the intensity ratio B1/G2 increases with increase in the intensity ratio R2/G2 (the contour line representing an oxygen saturation level of 0% ascends slantly), as shown in FIG. 7, is as follows. As described above, the blood volume increases with increase in the intensity ratio R2/G2, because of the correlation between the blood volume and the intensity ratio R2/G2. Out of the image data B1, G2, and R2, the green image data G2 decreases most largely with increase in the blood volume, and the blue image data B1 decreases next largely. This is because the absorption coefficient is higher in a wavelength range of 540 to 580 nm included in the green image data G2 than in a wavelength range of around 470 nm included in the blue image data B1 (see FIG. 8). Thus, as for the intensity ratio B1/G2, a pixel value of G2 being a denominator decreases more largely than a pixel value of B1 being a numerator, with increase in the blood volume. In other words, the intensity ratio B1/G2 increases with increase in the blood volume.

The oxygen saturation level calculator 86 calculates the oxygen saturation level of each pixel with the use of the correlation stored in the correlation memory 85 and the intensity ratios B1/G2 and R2/G2 calculated by the intensity ratio calculator 84. In the following description, B1*, G2*, and R2* represent intensity values of a certain pixel in the blue image data B1, the green image data G2, and the red image data R2, respectively, to be used in the calculation of the oxygen saturation level. More specifically, the intensity ratios of each pixel are represented by B1*/G2* and R2*/G2*.

Figure 9:
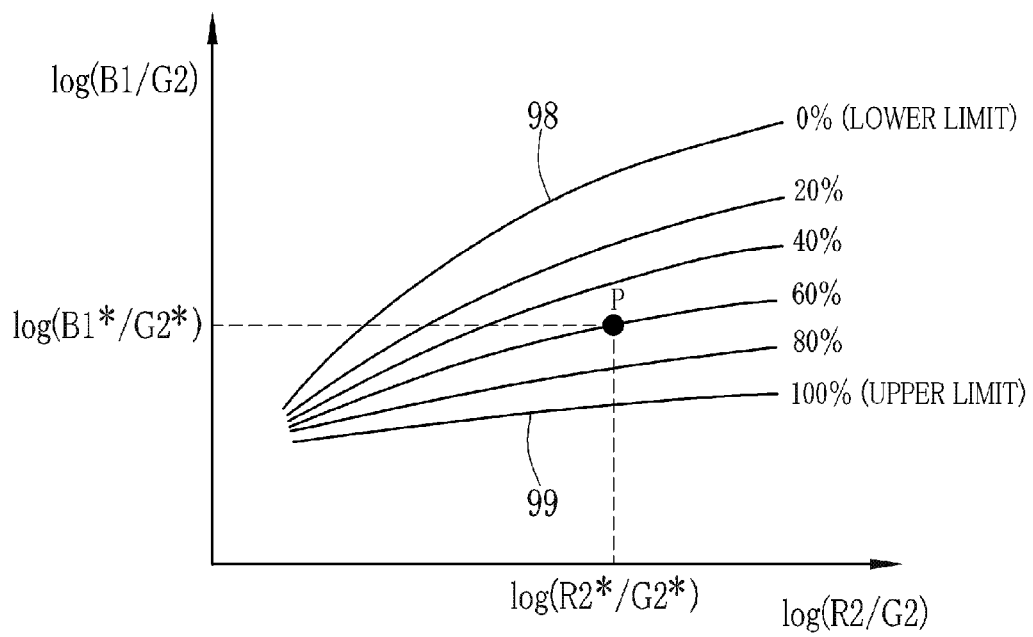
FIG. 9 is a graph for explaining a calculation method of the oxygen saturation level corresponding to intensity ratios $B1^*/G2^*$ and $R2^*/G2^*$ from the correlation of FIG. 7.

As shown in FIG. 9, the oxygen saturation level calculator 86 determines a point P corresponding to the intensity ratios B1*/G2* and R2*/G2* in the correlation stored in the correlation memory 85. When the point P is situated between a lower limit line 98 representing an oxygen saturation level of 0% and an upper limit line 99 representing an oxygen saturation level of 100%, the point P indicates the percentile of the oxygen saturation level. Taking FIG. 9 as an example, the point P is positioned in a contour line of 60%, so the oxygen saturation level is 60%.

If the point is out of a range between the lower and upper limit lines 98 and 99, and more specifically if the point is positioned above the lower limit line 98, the oxygen saturation level is determined to be 0%. If the point is positioned below the upper limit line 99, the oxygen saturation level is determined to be 100%. Note that, in a case where the point is out of the range between the lower and upper limit lines 98 and 99, the oxygen saturation level of that pixel may be judged to be unreliable and may not be displayed on the monitor device 14.

Figures 10, 11:
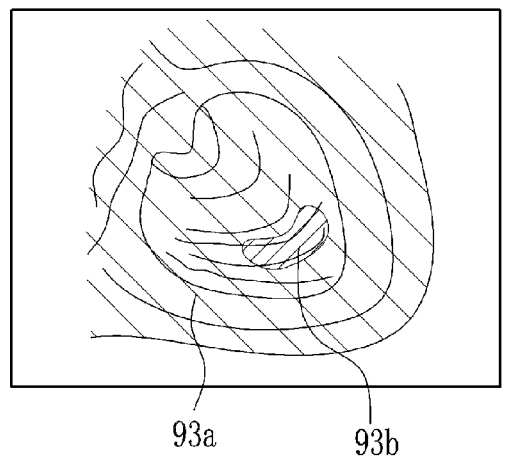
FIG. 10 is an explanatory view of a hyperoxic region and a hypoxic region in blue image data.
FIG. 11 is a table listing the contents of first to third region processes.

The region determiner 87 determines a hyperoxic region and a hypoxic region in the blue, green, and red image data B2, G2, and R2 obtained in the oxygen saturation level measurement mode based on the oxygen saturation level calculated by the oxygen saturation level calculator 86. The region determiner 87 determines a pixel area in which the oxygen saturation level equals or exceeds a certain value (for example, 60%) as the hyperoxic region, while determines a pixel area in which the oxygen saturation level is less than the certain value as the hypoxic region. Thus, as shown in FIG. 10, a hyperoxic region 93a and a hypoxic region 93b are determined in the blue image data B2. In a like manner, the hyperoxic and hypoxic regions are determined in the green and red image data G2 and R2.

The region processor 88 applies one of three different types of processes (region processes) to the hyperoxic and hypoxic regions of the blue, green, and red image data B2, G2, and R2. As shown in FIG. 11, the region processor 88 performs one of first to third region processes chosen by a user. In FIG. 11, a circle indicates performance of a process, and a cross indicates non-performance of a process. One of the first to third region processes is appropriately chosen by manual operation of the input device 15.

Figure 12:
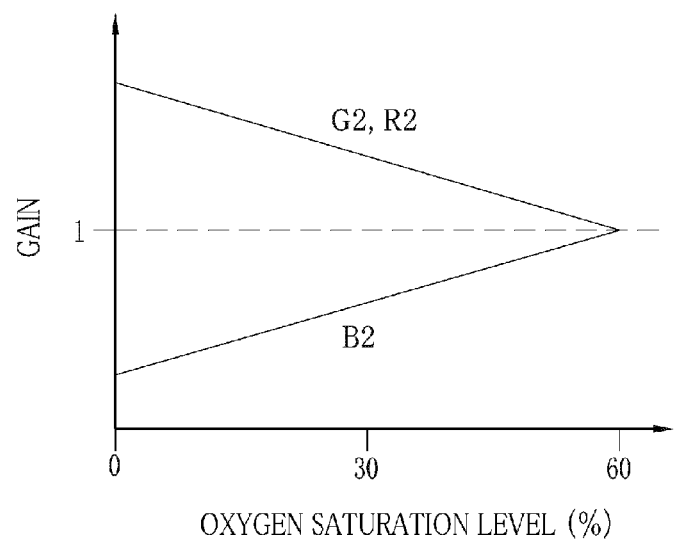
FIG. 12 is a graph showing the relation between the oxygen saturation level and a gain.

In the first region process, a gain process is applied to the hypoxic region, while neither a white balance (WB) process being a type of a color balance process nor a color enhancement process is applied thereto. In the gain process, as shown in FIG. 12, the pixel value of the blue image data B2 is decreased, and the pixel value of the green and red image data G2 and R2 is increased with decrease in the oxygen saturation level. In other words, the gain process disturbs the balance among the blue, green, and red image data B2, G2, and R2, contrarily to the WB process, which adjusts the balance of the image data of three colors. Therefore, the first region process brings about artificial color variations in accordance with difference in the oxygen saturation level. In the hypoxic region, color clearly differs between a portion having an oxygen saturation level of about 60% and a portion having an oxygen saturation level of about 40%.

Furthermore, according to the first region process, the WB process and the color enhancement process are applied to the hyperoxic region, while the gain process is not applied thereto. The WB process adjusts the balance among the blue, green, and red image data B2, G2, and R2. This improves the visibility of the internal body portion, including projections and depressions of living body tissue and a blood vessel pattern, and is effective for correct diagnosis. Note that, the WB process is carried out based on a correction value of the blue image data B2, a correction value of the green image data G2, and a correction value of the red image data R2 obtained by calibration performed before endoscopy.

Figure 13:
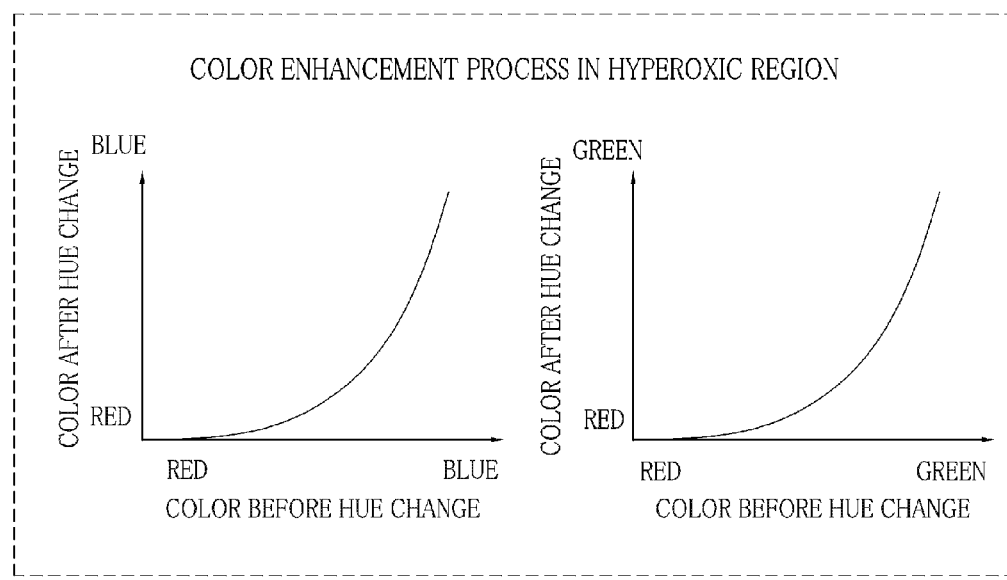
FIG. 13 is an explanatory view of a color enhancement process applied to the hyperoxic region.
Figure 14:
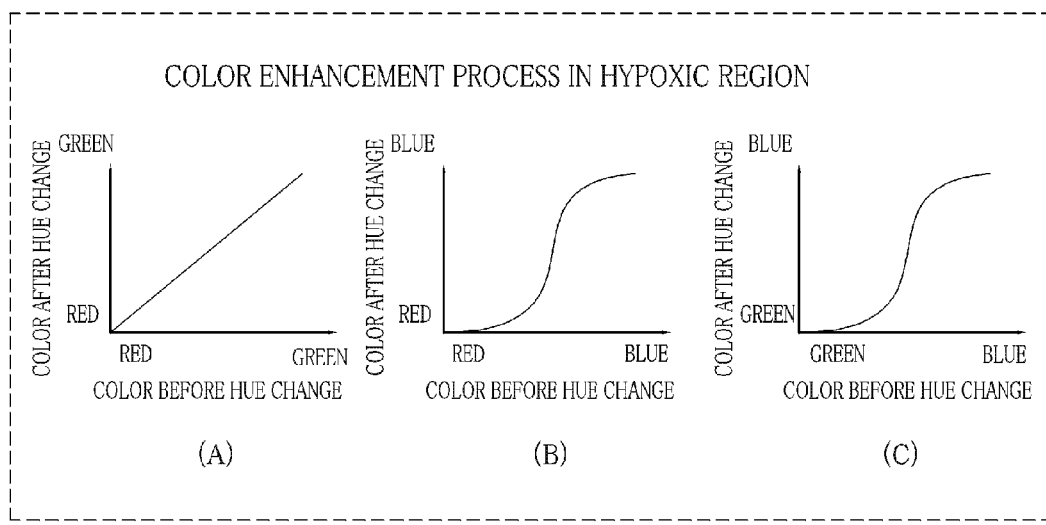
FIG. 14 is an explanatory view of the color enhancement process applied to the hypoxic region.

In addition to the WB process, the color enhancement process is applied to the hyperoxic region to enhance a red component. Since the interior of a human body is tinted red on the whole, the color enhancement process for enhancing red color further facilitates the visibility of the internal body portion, including the projections and depressions of the living body tissue and the blood vessel pattern. In this color enhancement process, the hyperoxic region of the blue, green, and red image data B2, G2, and R2 is converted into an HSI signal, and the HSI signal is subjected to a hue change process using tone curves of FIG. 13. By the hue change process, bluish and greenish color is tinged with red. The hue change process brings bluish and greenish color close to red. The HIS signal after the hue change process is subjected to RGB conversion again. Note that, the blue, green, and red image data after being subjected to the RGB conversion is also represented by B2, G2, and R2. In FIGS. 13 and 14, a horizontal axis of the tone curve represents "color before the hue change process", and a vertical axis represents "color after the hue change process".

As shown in FIG. 11, according to the second region process, the gain process and the color enhancement process are applied to the hypoxic region, while the WB process is not applied thereto. The gain process is the same as that of the first region process. After the gain process, the hypoxic region of the blue, green, and red image data B2, G2, and R2 is subjected to the color enhancement process, in order to make more distinct color variations in accordance with the difference of the oxygen saturation level. Therefore, even slight difference of the oxygen saturation level is reflected in the color variations.

In this color enhancement process, the hypoxic region of the blue, green, and red image data B2, G2, and R2 is converted into an HSI signal, and the HSI signal is subjected to the hue change process using tone curves of (A) to (C) of FIG. 14. In this hue change process, "red" and "green" that were multiplied by a gain of more than "1" are kept as is without changing its hue between "green" and "red", as shown in (A) of FIG. 14. As for "blue" that was multiplied by a gain of less than "1", on the other hand, a hue between "red" and "blue" and a hue between "green" and "blue" are changed, as shown in FIG. 14 (B) and (C). This prevents reddish and greenish color from being tinted blue as much as possible, and brings bluish color close to blue. The HSI signal after the hue change process is subjected to the RGB conversion again. The blue, green, and red image data after the RGB conversion is also represented by B2, G2, and R2.

In the second region process, the WB process is applied to the hyperoxic region, while neither the gain process nor the color enhancement process is applied thereto. The WB process applied to the hyperoxic region is the same as that of the first region process.

According to the third region process, as shown in FIG. 11, the gain process and the color enhancement process are applied to the hypoxic region, while the WB process is not applied thereto. The WB process and the color enhancement process are applied to the hyperoxic region, while the gain process is not applied thereto. The gain process and the color enhancement process applied to the hypoxic region are the same as those of the first and second region processes. The WB process and the color enhancement process applied to the hyperoxic region are the same as those of the first and second region processes.

Figure 15A:
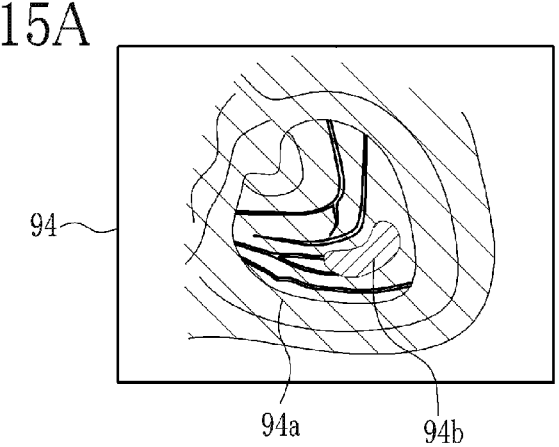
FIG. 15A is a schematic view showing an example of an oxygen saturation image subjected to the first region process.

After the region processor 88 applies one of the first to third region processes to the blue, green, and red image data B2, G2, and R2, the image generator 89 assigns the processed blue, green, and red image data B2, G2, and R2 to the B, G, and R channels of the monitor device 14, respectively. Thus, the oxygen saturation image is displayed on the monitor device 14. As shown in FIG. 15A, in an oxygen saturation image 94 subjected to the first region process, the projections and depressions of the living body tissue and the blood vessel pattern are more clearly visible in a hyperoxic region 94a than in a hyperoxic region of the normal image. A hypoxic region 94b of the oxygen saturation image 94 is displayed with artificial colors in accordance with the degree of the oxygen saturation level.

Figure 15B:
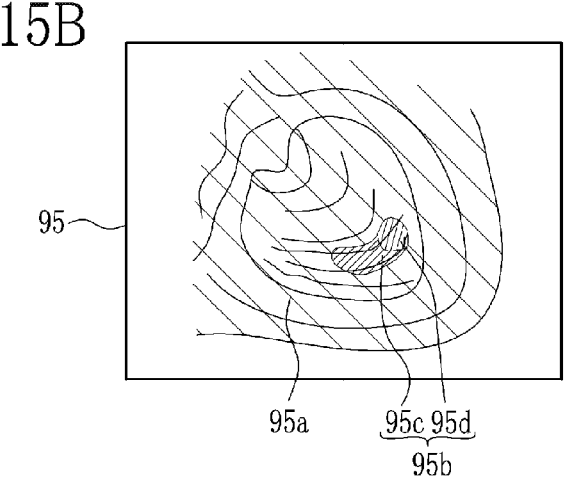
FIG. 15B is a schematic view showing an example of the oxygen saturation image subjected to the second region process.

As shown in FIG. 15B, in an oxygen saturation image 95 subjected to the second region process, a hyperoxic region 95a is of the same image quality as the normal image. A hypoxic region 95b of the oxygen saturation image 95 is subjected to the color enhancement process (artificial color enhancement process), so even the slight difference in the oxygen saturation level is reflected as the color variations, in contrast to the hypoxic region 94b of the oxygen saturation image 94. In the hypoxic region 95b, a portion 95c has an oxygen saturation level of 50 to 60%, and a portion 95d has an oxygen saturation level of 40 to 50%.

Figure 15C:
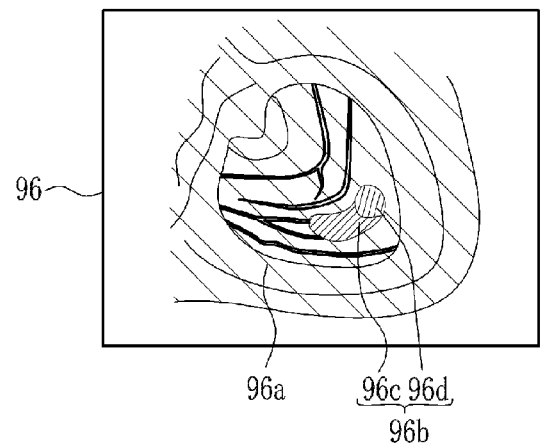
FIG. 15C is a schematic view showing an example of the oxygen saturation image subjected to the third region process.

As shown in FIG. 15C, in an oxygen saturation image 96 subjected to the third region process, the projections and depressions of the living body tissue and the blood vessel pattern are more clearly visible in a hyperoxic region 96a than that of the normal image. Also, a hypoxic region 96b of the oxygen saturation image 96 is subjected to the artificial color enhancement process, so even the slight difference in the oxygen saturation level is reflected as the color variations, in contrast to the hypoxic region 94b of the oxygen saturation image 94. In the hypoxic region 96b, a portion 96c has an oxygen saturation level of 50 to 60%, and a portion 96d has an oxygen saturation level of 40 to 50%.

Next, the operation in the oxygen saturation level measurement mode will be described with referring to a flowchart of FIG. 16. First, the endoscope system 10 is put into the oxygen saturation level measurement mode by operation of the mode switch 21 of the endoscope device 12, and one of the first to third region processes is chosen by operation of the input device 15. Thus, the color image sensor 60 captures images of the internal body portion alternately irradiated with the measurement light and the normal light, as shown in FIG. 5B.

After that, based on the obtained image data, the intensity ratio B1/G2 between the blue image data B1 and the green image data G2 and the intensity ratio R2/G2 between the red image data R2 and the green image data G2 are calculated on a pixel-by-pixel basis. The oxygen saturation level of each pixel is calculated from the two intensity ratios B1/G2 and R2/G2 and the correlation stored in the correlation memory 85. Based on the calculated oxygen saturation level, the hyperoxic and hypoxic regions are determined in the blue, green, and red image data B2, G2, and R2. One of the first to third region processes chosen through the input device 15 is applied to the blue, green, and red image data B2, G2, and R2. According to the chosen region process, at least one of the WB process, the gain process, and the color enhancement process are applied to each of the hyperoxic and hypoxic regions. The blue, green, and red image data B2, G2, and R2 after being subjected to the region process is assigned to the B, G, and R channels of the monitor device 14, respectively. Thus, the oxygen saturation image is displayed on the monitor device 14. The sequential steps from the application of the measurement and normal light to the display of the oxygen saturation image are repeated as long as the endoscope system 10 is in the oxygen saturation level measurement mode.

(Second Embodiment)

Figure 17:
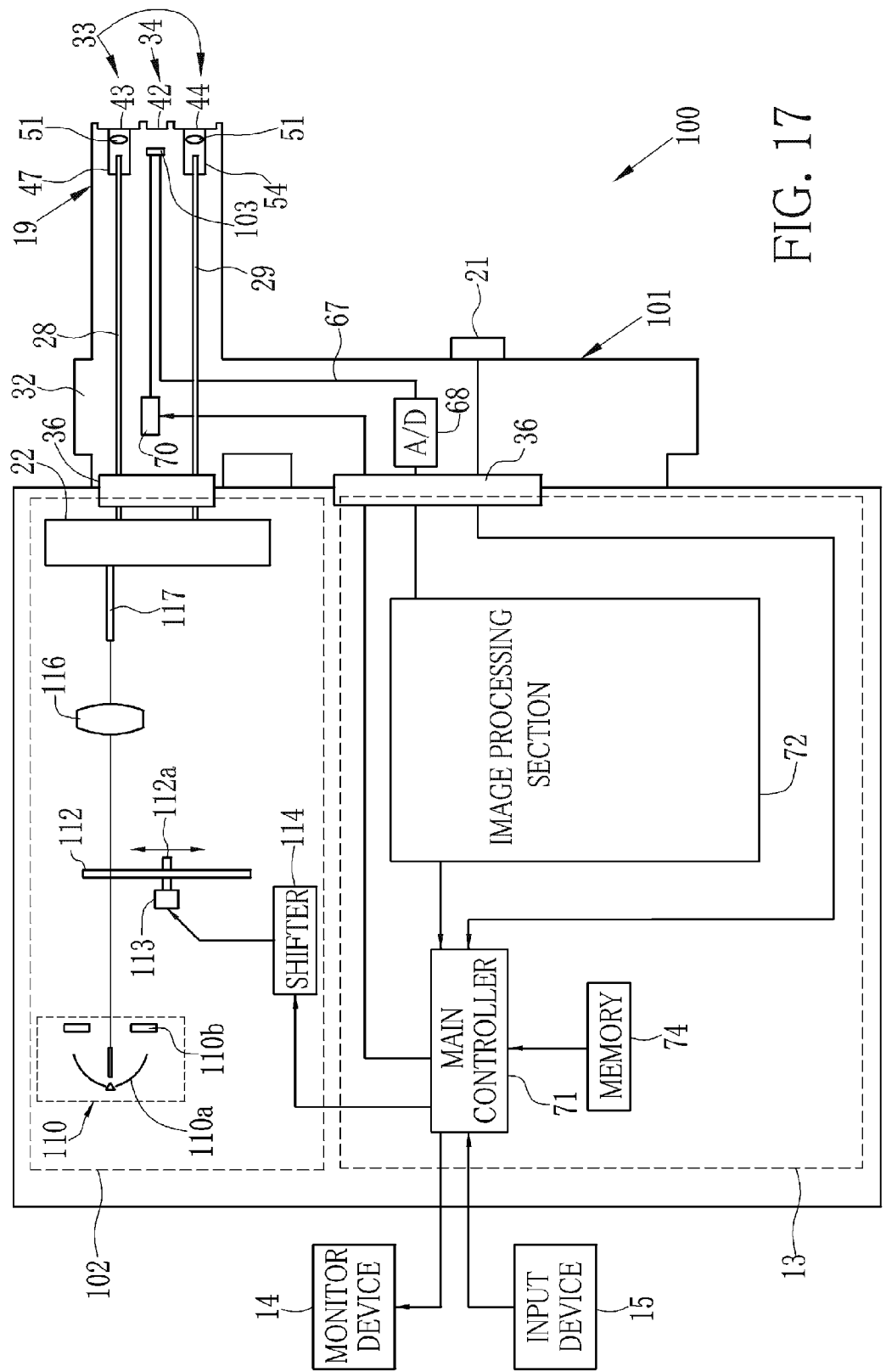
FIG. 17 is a block diagram of an endoscope system according to a second embodiment.

In the above first embodiment, semiconductor light sources are used for obtaining the illumination light. A second embodiment instead adopts a rotary filter method, which uses a white light source such as a xenon lamp and a rotary filter for performing wavelength separation of broad band light emitted from the white light source. As shown in FIG. 17, an endoscope system 100 according to the second embodiment has the same structure as the endoscope system 10, except for an endoscope device 101 and a light source device 102. Therefore, the structure of the endoscope device 101, the light source device 102, and related parts thereof will be described below, and explanation of the other parts will be omitted.

The endoscope device 101 differs from the endoscope device 12 in terms that there is no phosphor 50 in the lighting section 33. Thus, light led from the light source device 102 is directly applied to the internal body portion through the light guides 28 and 29. An image sensor 103 is a monochrome CCD having no color filter in its imaging surface, in contrast to the image sensor 60. As for the other components, the endoscope device 101 is identical to the endoscope device 12.

The light source device 102 includes a white light source 110, a rotary filter 112, a motor 113 connected to a rotary shaft 112a of the rotary filter 112, and a shifter 114. The white light source 110 emits broad band light BB having a wavelength band of 400 to 700 nm. The rotary filter 112 splits the broad band light BB emitted from the white light source 110 into light of a predetermined wavelength. The motor 113 rotates the rotary filter 112 at constant speed. The shifter 114 shifts the rotary filter 112 in its radial direction.

The white light source 110 includes a main body 110a for emitting the broad band light BB, and an aperture stop 110b for regulating the light amount of the broadband light BB. The main body 110a is composed of a xenon lamp, a halogen lamp, a metal halide lamp, or the like. The degree of opening of the aperture stop 110b is regulated by a light amount controller (not shown).

Figure 18:
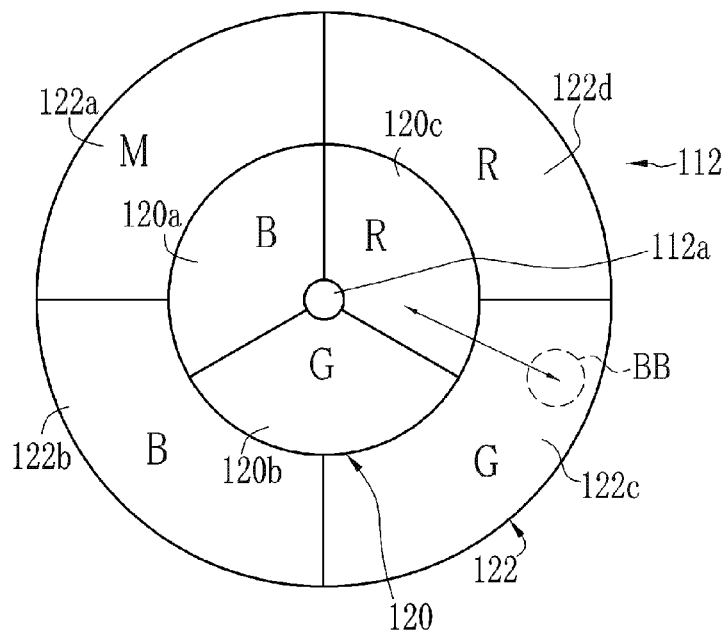
FIG. 18 is a plan view of a rotary filter.

As shown in FIG. 18, the rotary filter 112 rotates about the rotary shaft 112a connected to the motor 113. The rotary filter 112 is composed of a first filter portion 120 and a second filter portion 122 disposed in this order from the rotary shaft 112a being a rotation axis along the radial direction. The first filter portion 120 is set in an optical path of the broad band light BB in the normal mode. The second filter portion 122 is set in the optical path of the broad band light BB in the oxygen saturation level measurement mode. The shifter 114 shifts the rotary filter 112 in its radial direction to switch the positioning of the first and second filter portions 120 and 122.

Figure 19:
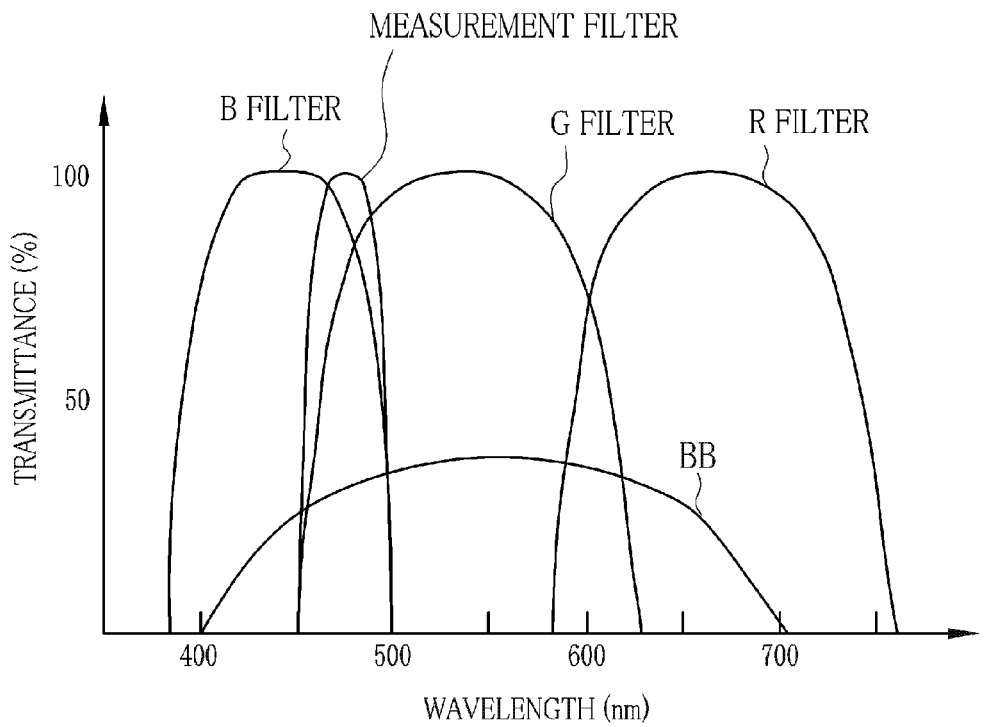
FIG. 19 is a graph showing spectral transmittance of measurement, B, G, and R filters.

The first filter portion 120 has a B filter 120a, a G filter 120b, and an R filter 120c each of which has the shape of a sector having a central angle of 120°. As shown in FIG. 19, the B filter 120a transmits B light having a blue wavelength band (380 to 500 nm) out of the broad band light BB. The G filter 120b transmits G light having a green wavelength band (450 to 630 nm) out of the broad band light BB. The R filter 120c transmits R light having a red wavelength band (580 to 760 nm) out of the broad band light BB. Thus, the B, G, and R light is sequentially emitted by the rotation of the rotary filter 112. The B, G, and R light enters the light guides 28 and 29 through a condenser lens 116 and an optical fiber 117.

The second filter portion 122 has a measurement filter 112a (represented by "M" in FIG. 18), a B filter 112b, a G filter 122c, and an R filter 122d. The measurement filter 122a transmits the measurement light for measuring the oxygen saturation level having a wavelength band of 450 to 500 nm out of the broad band light BB. The B filter 122b transmits the B light having the blue wavelength band (380 to 500 nm), just as with the above B filter 120a. The G filter 122c transmits the G light having the green wavelength band (450 to 630 nm), just as with the above G filter 120b. The R filter 122d transmits the R light having the red wavelength band (580 to 760 nm), just as with the above R filter 120c. Thus, the measurement, B, G, and R light is sequentially emitted by the rotation of the rotary filter 112. The four types of light enter the light guides 28 and 29 through the condenser lens 116 and the optical fiber 117.

Figure 20A:
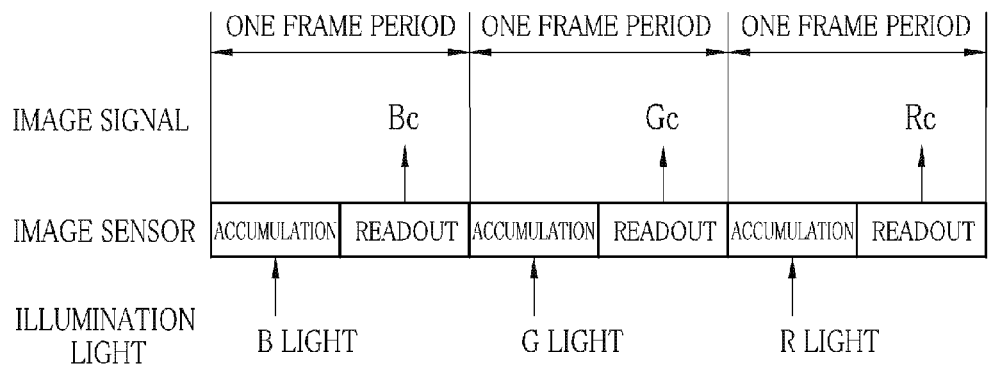
FIG. 20A is an explanatory view for explaining the operation of the image sensor in the normal mode according to the second embodiment.

Since the endoscope system 100 according to the second embodiment adopts the rotary filter method, the imaging control of the endoscope system 100 is different from that of the endoscope system 10. In the normal mode, as shown in FIG. 20A, the image sensor 103 images the internal body portion sequentially irradiated with the B, G, and R light. The image sensor 103 accumulates electric charge and sequentially outputs a blue signal, a green signal, and a red signal. This sequential operation is repeated as long as the endoscope system 100 is in the normal mode. The A/D converter 58 converts the blue signal into blue image data Bc, the green signal into green image data Gc, and the red signal into red image data Rc. The blue, green, and red image data Bc, Gc, and Rc is assigned to the B, G, and R channels of the monitor device 14, respectively. Thus, a normal image is displayed on the monitor device 14.

Figure 20B:
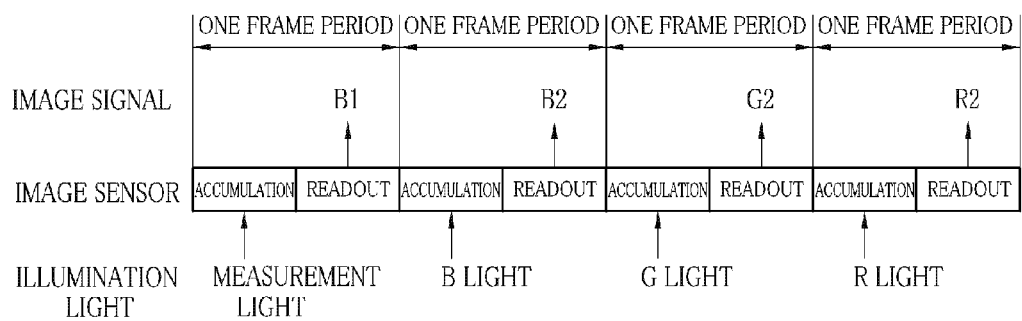
FIG. 20B is an explanatory view for explaining the operation of the image sensor in the oxygen saturation measurement mode according to the second embodiment.

In the oxygen saturation level measurement mode, as shown FIG. 20B, the image sensor 103 images the internal body portion sequentially irradiated with the measurement, B, G, and R light. The image sensor 103 accumulates electric charge and sequentially outputs a measurement blue signal, a blue signal, a green signal, and a red signal. This sequential operation is repeated as long as the endoscope system 100 is in the oxygen saturation level measurement mode. The A/D converter 58 converts the measurement blue signal into measurement blue image data B1, the blue signal into blue image data B2, the green signal into green image data G2, and the red signal into red image data R2. Note that, the blue image data B2, the green image data G2, and the red image data R2 correspond to first blue image data, first green image data, and first red image data, respectively, included in first image information. The measurement blue image data B1 corresponds to second blue image data included in second image information.

Out of the image data obtained in the oxygen saturation level measurement mode, the measurement blue image data B1, the green image data G2, and the red image data R2 are used for calculating the oxygen saturation level by the same procedure as described in the first embodiment. Based on the calculated oxygen saturation level, the hyperoxic and hypoxic regions are determined in the blue, green, and red image data B2, G2, and R2. One of the first to third region processes is applied to each of the hyperoxic and hypoxic regions. The blue, green, and red image data B2, G2, and R2 after being subjected to the region process is assigned to the B, G, and R channels of the monitor device 14. Thus, the oxygen saturation image is displayed on the monitor device 14.

In the first and second embodiments, as the color enhancement process, a red enhancement process is applied to the hyperoxic region, and a process for enhancing the color variations according to the difference in the oxygen saturation level is applied to the hypoxic region. However, a chroma enhancement process may be performed instead as the color enhancement process. The color enhancement process may be performed using a spectral image that is obtained by spectral estimation of the normal image (image obtained from the blue, green, and red image data B2, G2, and R2).

Note that, the phosphor 50 is contained in the head assembly 19 in the first embodiment, but may be provided in the light source device 11 instead. In this case, the phosphor 50 is necessarily provided between the LD2 (445 nm) and the optical fiber 25. No phosphor 50 may be provided between the LD1 (473 nm) and the optical fiber 24.

In the above first and second embodiments, the oxygen saturation image is produced using the oxygen saturation level, which is the ratio of oxyhemoglobin to blood volume (the sum of oxyhemoglobin and deoxyhemoglobin). Instead of or in addition to this, the oxygen saturation image may be produced using an oxyhemoglobin index calculated by "blood volume×oxygen saturation level (%)" or a deoxyhemoglobin index calculated by "blood volume×(100-oxygen saturation level) (%)".

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
   a lighting section for applying illumination light to an object, broad band light in a visible range and narrow band light having a wavelength range in which oxyhemoglobin and deoxyhemoglobin have different absorption coefficients being used as said illumination light;
   an image information obtaining section for imaging said object under irradiation with said broad band light to obtain first image information, and imaging said object under irradiation with said narrow band light to obtain second image information;

a normal image producing section for producing a normal image having a wavelength component of said broad band light based on said first image information;

an oxygen saturation level calculator for calculating an oxygen saturation level of blood based on said second image information;

a region determiner for determining in said normal image a hyperoxic region having said oxygen saturation level of a predetermined value or more and a hypoxic region having said oxygen saturation level of less than said predetermined value; and a region processor for applying a different type of process to each of said hyperoxic region and said hypoxic region, and producing an oxygen saturation image, wherein said region processor applies a color balance process to said hyperoxic region to adjust color balance, and applies a gain process to said hypoxic region to bring about color variations in said hypoxic region in accordance with difference in said oxygen saturation level, wherein said region processor applies said color balance process to said hyperoxic region without applying said gain process to said hyperoxic region, and applies said gain process to said hypoxic region without applying said color balance process to said hypoxic region, wherein said region processor applies a different type of color enhancement process to each of said hyperoxic region and said hypoxic region by applying a different tone curve to each of said hyperoxic region and said hypoxic region, and wherein said region processor applies said color enhancement process to one or both of said hyperoxic region and said hypoxic region according to an input from an input device.

2. The endoscope system according to claim 1, further comprising a monitor device for displaying said normal image or said oxygen saturation image.

3. The endoscope system according to claim 2, wherein said color balance process adjusts white balance in said hyperoxic region by adjustment of a pixel value of said hyperoxic region;

said gain process varies color in said hypoxic region in accordance with a degree of said oxygen saturation level by adjustment of said pixel value of said hypoxic region; and wherein said region processor applies a white balance process and a color enhancement process for enhancing a red component to said hyperoxic region, and applies an artificial color enhancement process for enhancing artificial colors to said hypoxic region, which is tinged with artificial colors different in accordance with a degree of said oxygen saturation level, without applying said white balance process to said hypoxic region.

4. The endoscope system according to claim 2, wherein said region processor applies a color enhancement process to at least one of said hyperoxic region and said hypoxic region.

5. The endoscope system according to claim 4, wherein said color enhancement process to be applied to said hyperoxic region is a red color enhancement process for enhancing a red component.

6. The endoscope system according to claim 4, wherein said hypoxic region is tinged with artificial colors different in accordance with said degree of said oxygen saturation level, and said color enhancement process to be applied to said hypoxic region is an artificial color enhancement process for enhancing said artificial colors.

7. The endoscope system according to claim 2, wherein said image information obtaining section includes a color image sensor;

said first image information includes first blue image data, first green image data, and first red image data, and said color image sensor images said object under irradiation with first blue narrow band light of 440 to 460 nm and fluorescence produced by wavelength conversion of said first blue narrow band light by a wavelength conversion element, and B pixels, G pixels, and R pixels of said color image sensor produce said first blue, green, and red image data, respectively; and said second image information includes second blue image data, and said color image sensor images said object under irradiation with second blue narrow band light of 460 to 480 nm and fluorescence produced by wavelength conversion of said second blue narrow band light by said wavelength conversion element, and said B pixels of said color image sensor produce said second blue image data.

8. The endoscope system according to claim 2, wherein said image information obtaining section includes a monochrome image sensor;

said first image information includes first blue image data, first green image data, and first red image data, and said monochrome image sensor images said object sequentially irradiated with blue light, green light, and red light to obtain said first blue image data, said first green image data, and said first red image data, respectively; and said second image information includes second blue image data, and said monochrome image sensor images said object under irradiation with blue light of 450 to 500 nm to obtain said second blue image data.

9. The endoscope system according to claim 7, wherein said oxygen saturation level calculator calculates said oxygen saturation level based on said second blue image data, said first green image data, and said first red image data.

10. A processor device of an endoscope system, said endoscope system including a lighting section for applying illumination light to an object and an image information obtaining section for obtaining first and second image information, broad band light in a visible range and narrow band light having a wavelength range in which oxyhemoglobin and deoxyhemoglobin have different absorption coefficients being used as said illumination light, said first image information being obtained by imaging said object under irradiation with said broad band light, and said second image information being obtained by imaging said object under irradiation with said narrow band light, said processor device comprising:

a reception section for receiving said first and second image information;

a normal image producing section for producing a normal image having a wavelength component of said broad band light based on said first image information;

an oxygen saturation level calculator for calculating an oxygen saturation level of blood based on said second image information;

a region determiner for determining in said normal image a hyperoxic region having said oxygen saturation level of a predetermined value or more and a hypoxic region having said oxygen saturation level of less than said predetermined value; and a region processor for applying a different type of process to each of said hyperoxic region and said hypoxic region, and producing an oxygen saturation image, wherein said region processor applies a color balance process to said hyperoxic region to adjust color balance, and applies a gain process to said hypoxic region to bring about color variations in said hypoxic region in accordance with difference in said oxygen saturation level, wherein said region processor applies said color balance process to said hyperoxic region without applying said gain process to said hyperoxic region, and applies said gain process to said hypoxic region without applying said color balance process to said hypoxic region, wherein said region processor applies a different type of color enhancement process to each of said hyperoxic region and said hypoxic region by applying a different tone curve to each of said hyperoxic region and said hypoxic region, and wherein said region processor applies said color enhancement process to one or both of said hyperoxic region and said hypoxic region according to an input from an input device.

11. An image processing method of an endoscope system including a lighting section for applying illumination light to an object and an image information obtaining section for obtaining first and second image information, broad band light in a visible range and narrow band light having a wavelength range in which oxyhemoglobin and deoxyhemoglobin have different absorption coefficients being used as said illumination light, said first image information being obtained by imaging said object under irradiation with said broad band light, and said second image information being obtained by imaging said object under irradiation with said narrow band light, said image processing method comprising the steps of:

producing a normal image having a wavelength component of said broad band light based on said first image information;

calculating an oxygen saturation level of blood based on said second image information;

determining in said normal image a hyperoxic region having said oxygen saturation level of a predetermined value or more and a hypoxic region having said oxygen saturation level of less than said predetermined value;

applying a different type of process to each of said hyperoxic region and said hypoxic region, and producing an oxygen saturation image;

applying a color balance process to said hyperoxic region to adjust color balance;

applying a gain process to said hypoxic region to bring about color variations in said hypoxic region in accordance with difference in said oxygen saturation level and applying a different type of color enhancement process to each of said hyperoxic region and said hypoxic region by applying a different tone curve to each of said hyperoxic region and said hypoxic region, wherein said region processor applies said color balance process to said hyperoxic region without applying said gain process to said hyperoxic region, and applies said gain process to said hypoxic region without applying said color balance process to said hypoxic region, and wherein said region processor applies said color enhancement process to one or both of said hyperoxic region and said hypoxic region according to an input from an input device.

* * * * *

UNITED STATES PATENT AND TRADEMARK OFFICE
CERTIFICATE OF CORRECTION

| | | |
|---|---|---|
| PATENT NO. | : 9,565,399 B2 | Page 1 of 1 |
| APPLICATION NO. | : 14/013301 | |
| DATED | : February 7, 2017 | |
| INVENTOR(S) | : Masahiro Kubo | |

It is certified that error appears in the above-identified patent and that said Letters Patent is hereby corrected as shown below:

On the Title Page

Insert the following:

-- (30) Foreign Application Priority Data

Sep. 5, 2012    (JP) .................... 2012-195097 --.

Signed and Sealed this
Sixteenth Day of May, 2017

Michelle K. Lee
*Director of the United States Patent and Trademark Office*